United States Patent [19]

Packard

[11] Patent Number: 4,995,473

[45] Date of Patent: Feb. 26, 1991

[54] STETHOSCOPE WITH DIAPHRAGM HEAD ADAPTER

[75] Inventor: Thomas J. Packard, Somerset, Wis.

[73] Assignee: Minnesota Mining and Manufacturing Company, St. Paul, Minn.

[21] Appl. No.: 454,178

[22] Filed: Dec. 21, 1989

[51] Int. Cl.⁵ .............................................. A61B 7/02
[52] U.S. Cl. .................................. 181/137; 181/132; 181/137
[58] Field of Search ............... 181/130, 131, 132, 137, 181/158

[56] References Cited

U.S. PATENT DOCUMENTS

| | | | |
|---|---|---|---|
| 2,513,985 | 7/1950 | Woodruff et al. | 181/130 X |
| 2,529,562 | 12/1950 | Martin | 181/137 X |
| 3,223,195 | 12/1965 | Allen | 181/137 |
| 3,366,198 | 1/1968 | Littmann | 181/137 |
| 3,601,218 | 8/1971 | Reynolds, Jr. | 181/137 |
| 4,200,169 | 4/1980 | MacDonald, III et al. | 181/131 |
| 4,440,258 | 4/1984 | Packard | 181/137 |
| 4,475,619 | 10/1984 | Packard | 181/137 |
| 4,502,562 | 3/1985 | Nelson | 181/131 |

Primary Examiner—Benjamin R. Fuller
Attorney, Agent, or Firm—Donald M. Sell; Walter N. Kirn; John H. Hornickel

[57] ABSTRACT

A stethoscope head adapter for a diaphragm microphone is provided. The adapter creates a smaller surface area for the diaphragm microphone without diminishing the acoustical reception by the diaphragm of normal or pathological conditions in a patient. The adapter is made from an elastomeric material to permit easy placement on the stethoscope head and to provide an effective acoustical seal against the uneven surface of the skin of a patient. A secondary diaphragm may also be provided in the adapter to focus the reception by the diaphragm microphone of the specific frequencies desired to be monitored. With the adapter on the stethoscope head, the intensities of sound at frequencies not desired to be monitored are attenuated when compared with the use of the stethoscope head without the adapter present.

21 Claims, 3 Drawing Sheets

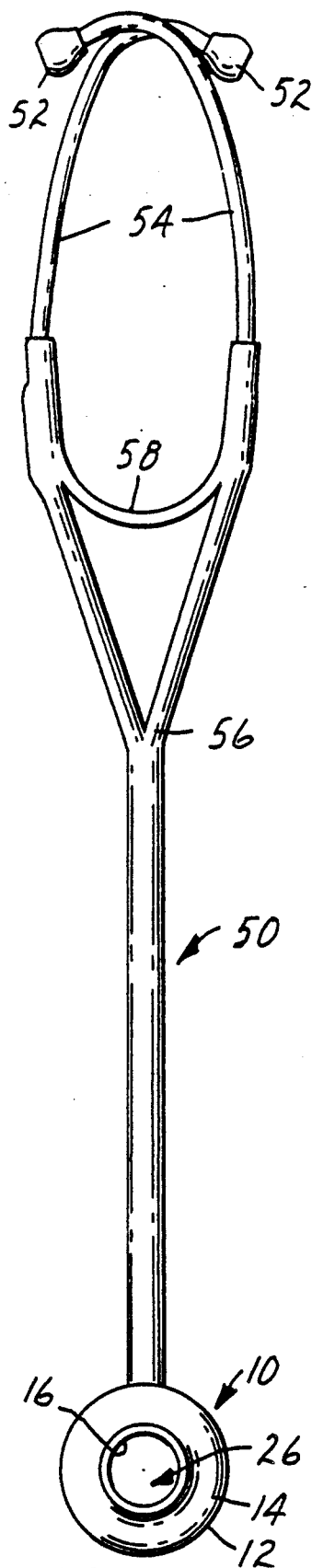
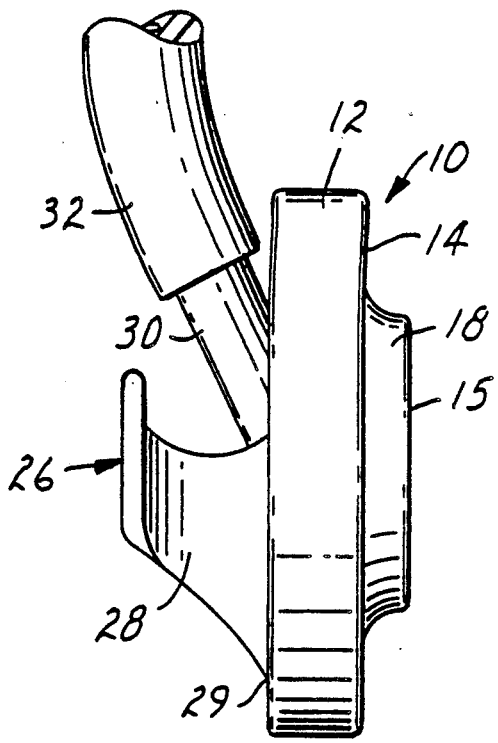
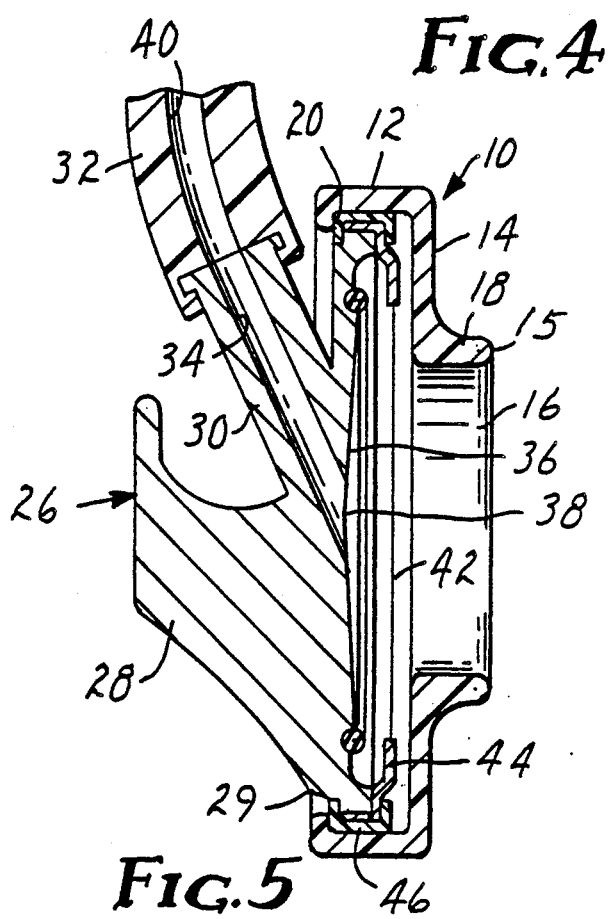

STETHOSCOPE WITH DIAPHRAGM HEAD ADAPTER

FIELD OF THE INVENTION

This invention relates to stethoscopes and adapters to be used with diaphragm heads of such stethoscopes.

BACKGROUND OF THE INVENTION

A modern acoustical stethoscope typically has a head having a microphone containing a diaphragm. Some stethoscopes combine in the head both a diaphragm microphone and a bell microphone.

The acoustical stethoscope is used to diagnose the condition of a patient based on the acoustical output from the body of the patient. The frequency of the body's acoustical output is in the very low range of normal human hearing and less than the 3,000 Hertz (Hz) frequency where humans perceive sounds most strongly.

For example, the acoustic output from the heart has a spectrum from about the threshold of hearing to about 175 Hz corresponding to the normal opening and closing of the heart valves. Diagnosis of pathological conditions such as murmurs or clicks occurs in the acoustical spectrum from the heart of from about 200 Hz to about 350 Hz, with occasional pathological states presenting acoustic energy in somewhat higher ranges, e.g. to about 650 Hz.

Unfortunately, the threshold of audibility of a sound at a given frequency varies widely in the presence of other sounds from which it must be discriminated. Often, a sound of a lower frequency through its acoustic overtones can mask a sound of a higher frequency. Masking of the pathological heart sounds in the region of 200-350 Hz by the normal heart sounds at lower frequencies has been reduced by providing a diaphragm in the microphone of a stethoscope which attenuates the low frequency, normal heart sounds while transmitting the higher frequency, pathological condition sounds.

The diaphragm microphone of stethoscope heads has been constructed to overcome the effects of masking by providing a head which permits the diaphragm to move among several positions, such as that disclosed in U.S. Pat. No. 3,223,195; a diaphragm which floats in the microphone, such as that disclosed in U.S. Pat. No. 4,475,619; and a diaphragm against which pressure is applied to tune acoustical reception, such as that disclosed in U.S. Pat. No. 4,440,258.

While such diaphragm microphone constructions seek to provide refined or tuned acoustical transmission of the condition of a patient, some patients are difficult to diagnose because the surface area of the skin where the stethoscope head is placed does not provide continuous contact for the surface area of the diaphragm. Neonatal, pediatric, and emaciated patients are examples of such patients.

Incomplete contact between the diaphragm microphone and the surface of the skin can result in extraneous noise in those frequencies where the acoustical output of pathological conditions may be found. Reducing the sound leakage on the open bell microphone of a stethoscope head is known, such as that disclosed in U.S. Pat. No. 4,502,562. But a diaphragm microphone has a larger surface area typically than an open bell microphone and the sound receiving surface area of the diaphragm must remain flexible for proper acoustical receipt of the acoustical output of the body of the patient. Generally, it has been believed that a diaphragm microphone constructed to receive certain frequencies while relatively attenuating others did not need any further adjustment to its acoustical performance.

However, what is needed in the art is a structure to adapt the diaphragm microphone of a head to reduce the effects of loss of surface contact with the patient without affecting the ability of the diaphragm to receive the acoustical output from the body of the patient at the critical frequencies necessary for diagnosis.

SUMMARY OF THE INVENTION

The present invention solves the problems unsolved by the prior art by providing an adapter to be releasably engaged with the diaphragm microphone portion of a stethoscope head about the perimeter of the diaphragm body in a manner which effectively reduces the surface area of the diaphragm microphone contacting the skin of the patient. The adapter releasably engages the perimeter of the microphone body at an edge portion and covers the diaphragm sound receiving surface area up to a rim which defines a central opening of the adapter having an area less than the sound receiving surface area of the diaphragm.

The invention also provides an adapter which may have a secondary diaphragm across the central opening which assists in the relative attenuation of background noise otherwise affecting the diagnosis of a patient.

The invention also provides a stethoscope having a sound receiving head having sound transmitting lumens connected thereto and the adapter described herein which defines a central opening having an area less than the sound receiving surface area of the diaphragm microphone of the head.

It is an object of the invention to provide a releasably engaging adapter to be used on the diaphragm microphone portion of a stethoscope head when the surface area of the diaphragm microphone is likely to exceed the surface area of the body of a patient available for proper body sound transmission.

It is also an object of the invention to provide an adapter to the diaphragm microphone of a stethoscope head which is resilient and deformable to permit facile engagement of the adapter to the diaphragm microphone body and to enhance body surface contact with the patient.

It is another object of the invention to provide an adapter which defines a central opening about a raised boss in order to provide a good acoustical seal between the adapter and the skin of the patient, whether used with a "tunable" stethoscope in either high or low frequency mode, or used with a combination bell microphone/diaphragm microphone head.

A feature achieved by the adapter of the present invention is the proper sound transmission of the acoustical output of the body of a patient in those frequencies where pathological conditions are indicated while attenuating the frequencies of noise and other extraneous sounds at other frequencies which can distract or otherwise obfuscate the proper diagnosis of a patient.

Another feature of the invention is the construction of the adapter used in the present invention to be flexible to provide a good seal even as pressure is applied against a head which contains a "tunable" diaphragm microphone.

A more detailed description of the invention follows in reference to the drawing.

BRIEF DESCRIPTION OF THE DRAWING

FIG. 4 illustrates a stethoscope head having an adapter engaging the diaphragm microphone portion thereof.

FIG. 5 is a cross-sectional view of the stethoscope head and adapter of FIG. 4.

FIG. 6 illustrates a stethoscope having a head having an adapter engaging the diaphragm microphone portion thereof.

EMBODIMENTS OF THE INVENTION

Figure 1:
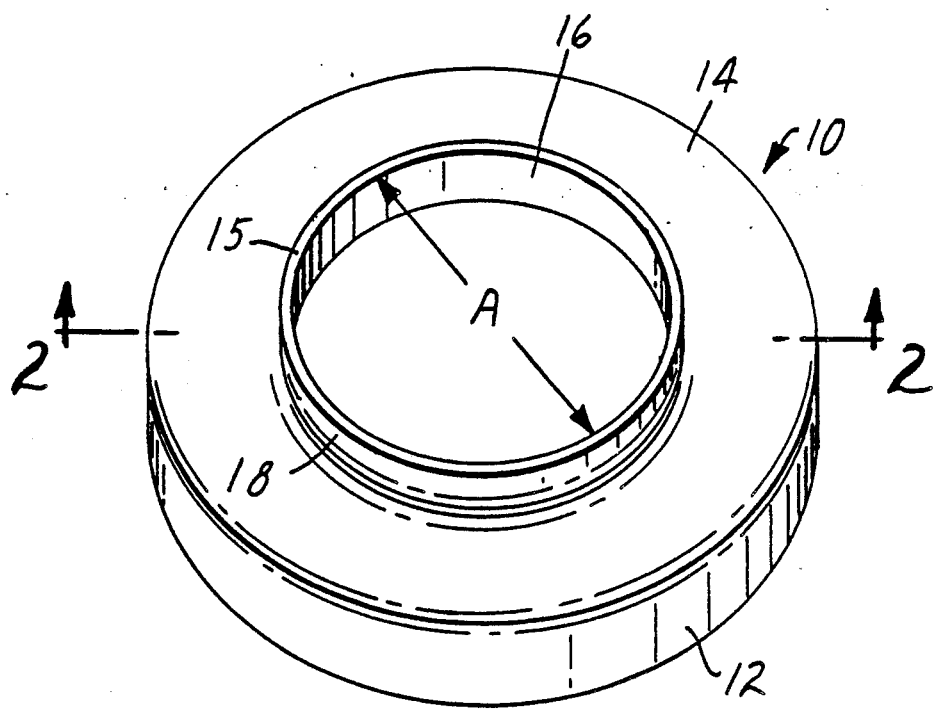
FIG. 1 illustrates a perspective view of an adapter useful according to the present invention.

Referring to FIG. 1, a perspective view of an adapter used with the present invention is illustrated. The adapter 10 has an edge portion 12 for releasably engaging to the perimeter of the microphone body of the stethoscope head and a cover portion 14 extending from the edge portion 12. The cover portion 14 terminates at a rim 15 which defines a central opening 16 having an area A. The size of area A of central opening 16 may be chosen by one skilled in the art relative to the surface area of the diaphragm microphone to which the adapter 10 engages and the size of the surface area of the patient's skin to which the head with the adapter 10 is likely to contact to provide an effective acoustical seal.

To further provide an effective acoustical seal, desirably, rim 15 comprises a raised boss 18 extending from the cover portion 14.

Figure 2:
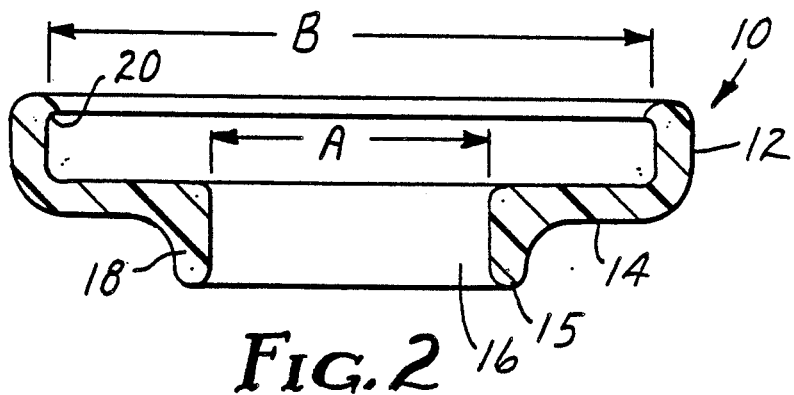
FIG. 2 illustrates a cross-sectional view of the adapter of FIG. 1 along lines 2—2.

Referring to FIG. 2, a cross-sectional view of FIG. 1 is provided and more clearly shows that edge portion 12 may have an annular lip 20 to provide a more effective releasable engagement of the adapter 10 to the perimeter of the microphone body of the stethoscope head. This cross-sectional view of FIG. 2 also demonstrates the reduction in surface area of the stethoscope head by comparing the size of area A representing the area of central opening 16 compared with the size of area B corresponding to the surface area of the sound receiving diaphragm which the adapter 10 covers.

Figure 3:
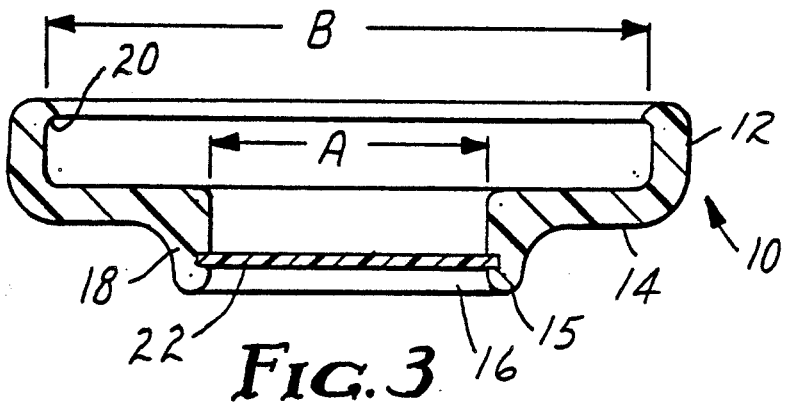
FIG. 3 illustrates a cross-sectional view of a second embodiment of the adapter useful according to the present invention.

Referring to FIG. 3, an alternate embodiment of the adapter of the present invention is shown. Spanning the central opening 16 is a secondary diaphragm 22 which resides in annular bore 24 in raised boss 18. The size of the central opening 16, and hence the surface exposure of secondary diaphragm 22 may permit the fine tuning of the diaphragm microphone to a specific frequency known to be where pathological conditions emit sound.

Referring to FIG. 4, a side view of a tunable stethoscope with an adapter of FIG. 1 is illustrated. The tunable stethoscope has a construction corresponding to the tunable stethoscope described in U.S. Pat. No. 4,440,258, the disclosure of which is incorporated by reference as if fully rewritten herein. The tunable stethoscope has a head 26 comprising a body 28 having a perimeter 29, and a stem 30 to which is connected elongated flexible tubing 32, such as that described in U.S. Pat. No. 4,200,169, the disclosure of which is incorporated by reference as if fully rewritten herein, and ear tubes with ear tips (not shown).

Referring to FIG. 5, the cross-sectional view of the stethoscope head 26 is seen. As was described in U.S. Pat. No. 4,400,258, the stem 30 has a bore 34 in communication with microphone 36 having a central aperture therein. Flexible tubing 32 has lumens 40, such as that disclosed in U.S. Pat. No. 4,200,169. The microphone has a diaphragm 42 attached thereto, covering the surface of the microphone 36. Thus, sound received by the surface area of diaphragm 42 is transmitted through aperture 38, bore 34, and lumens 40 to the ears of the listener.

While the adapter of the present invention is described in FIGS. 4 and 5 with respect to the stethoscope head of a tunable stethoscope such as that described in U.S. Pat. No. 4,440,258, the adapter 10 is useful with any stethoscope head having a diaphragm microphone and a perimeter on the body of the head which permits releasable engagement of the adapter 10 to such perimeter. For example, the adapter 10 may be used with the diaphragm microphone portion of a stethoscope head shown in U.S. Pat. No. 4,475,619, the disclosure of which is incorporated by reference as if fully rewritten herein.

Referring again to FIG. 5, an explanation of the construction of the tunable stethoscope head 26 may be completed. The diaphragm 42 is suspended by a compliant ring 44 which is held captured against the microphone body 28 by a retaining ring 46. In this instance, ring 46 serves as the periphery of the stethoscope head body 28 against which edge portion 12 of adapter 10 is releasably engaged and over which annular 20 secures the contacts.

An adapter releasably engaged to a stethoscope is fully illustrated in FIG. 6. The adapter 10 on the head 26 of a stethoscope 50 is seen. Stethoscope 50 has ear tips 52 on ear tubes 54 which join at a yoke junction 56 where a leaf spring 58 resides. Binaural tubing 32 connects the stethoscope head 26 with ear tubes 54. Adapter 10 is releasably engaged to head 26.

Adapter 10 may be made from a single material or may be combined from diverse materials, e.g., one material for use as the edge portion 12 and another material for use as the cover portion 14 and raised boss 18.

The edge portion of adapter 10 may be made from any material which permits it to releasably engage edge portion 12 with the microphone body 28, e.g., using a press fit or a snap fit. Use of either a metallic or nonmetallic material which is strong and resilient aids to provide an annular lip 20 which stretches over perimeter 29 during its releasable engagement.

The cover portion 14 and raised boss 18 of the adapter 10 may be made from any material which is deformable, comfortable and inert when in contact with human skin. Use of a non-metallic material aids to reduce the "chill" when the stethoscope head 26 contacts the skin for diagnosis.

Desirably, at least the cover portion 14 and raised boss 18 of the adapter 10 are made from one or more elastomeric materials which are resistant to repeated contact with oils present on the human skin. Urethane or silicone elastomers are particularly suited for fabrication into adapter 10.

Adapter 10 should be resilient and deformable. Using the durometer scale of hardness-softness defined by the Shore system of measurement and adopted as ASTM Standard D2240, on the Shore A scale, the adapter 10 should have a durometer ranging from 10 Shore A to about 90 Shore A. This permits adapter 10 to be fabricated from a variety of elastomeric materials known to those skilled in the art to provide flexibility for releasable engagement to the stethoscope perimeter 29 while also be conformable to the non-uniform surface of the skin of the patient being evaluated.

Desirably, for an effective acoustic seal, adapter 10 may be made from an elastomeric material having a Shore A durometer between about 20 Shore A and about 80 Shore A. It has been found that within this range, it is preferred to have adapter 10 fabricated from elastomeric materials having a Shore A durometer between about 35 Shore A and 75 Shore A.

Alternatively, the cover portion 14 and raised boss 18 may have the Shore A durometer values identified for adapter 10 above, while a different material serving as edge portion 12 and annular lip 20 may have a Shore A durometer value exceeding 90 Shore A.

The adapter 10 of the present invention may be manufactured by a variety of techniques known to those skilled in the art, such as liquid casting, compression molding, and injection molding. Manufacturing efficiencies are achieved when injection molding is used as the method of manufacturing the adapter 10 made of an elastomeric material. When adapter is made of more than one material, e.g., an edge portion 12 of a harder Shore A material and as cover portion 14 of a softer Shore A material, the two portions 12 and 14 may be joined, using adhesives, sonic welding, and the like.

Referring again to FIG. 3, the secondary diaphragm 22 may be constructed from any desirable diaphragm material known to those skilled in the art such as that disclosed in U.S. Pat. No. 4,440,258 or U.S. Pat. No. 4,475,619. As stated in the former, a preferred diaphragm comprises a 10 mil-thick (0.025 cm-thick) epoxy resin-fiberglass laminate.

The construction of stethoscope head 26, flexible tubing 32, and other components 52, 54, and 58 of the stethoscope 50 are also known to those skilled in the art, such as that disclosed in U.S. Pat. Nos. 4,440,258; 4,475,619; and 4,200,169.

The stethoscope 50 using the adapter 10 according to the present invention provides an effective acoustic seal at a smaller surface area than that provided by the diaphragm microphone. This results in attenuation of sound at frequencies which distract from the proper diagnosis of pathological conditions at other frequencies not attenuated by the adapter. Because the adapter 10 may be releasably engaged with the perimeter 29 of the microphone body 28, one may easily place the adapter 10 on the stethoscope 50 when the perceived need for attenuating sound at other frequencies arises.

While the use of the adapter 10 with the stethoscope 50 may be particularly beneficial in cases involving patients having limited and particularly uneven surface areas of skin where the acoustic diagnosis is to be made, it is to be understood that the use of adapter 10 is not so limited. Indeed, there is no perceived detriment to using adapter 10 in conjunction with the diagnosis of patients of all sizes and shapes and pathological conditions.

Careful selection of the size of the central opening 16 and use of secondary diaphragm 22 may further enhance the acoustical reception of sounds emanating from the body in a manner not presently used or foreseen in the art of acoustic diagnosis. For example, it may be possible through the selection of the geometry of the adapter 10, the surface area A size, the geometry of the central opening 16, the surface area of the optional secondary diaphragm 22, and the materials used to fabricate adapter 10 and diaphragm 22, to focus the acoustical reception of the stethoscope 50 and its diaphragm microphone 36 to a specific frequency range while attenuating other undesired frequency ranges.

While embodiments of the invention have described, the following examples further demonstrate the utility of the present invention.

EXAMPLE 1

An adapter having the geometry shown in FIG. 1 was fabricated by liquid casting the adapter at room temperature into an elastomeric mold. A urethane female mold (having a durometer of about 40 Shore A) was liquid cast from "TDT-178-34" urethane casting resin commercially available from Ren Plastics of East Lansing, Mich. around an aluminum male mold formed according to the geometry of the adapter desired. After hardening at room temperature, the female mold was cut open to extract the male mold. The halves of the female mold were filled with "RP 6401" urethane casting resin commercially available also from Ren Plastics and pressed together. After hardening at room temperature for about 12 hours, the adapter was removed from the mold. The durometer of the adapter was measured according to ASTM Standard D2240 using Shore A durometer. The durometer of the adapter was measured to be 70 Shore A.

EXAMPLE 2

An adapter was fabricated according to the manufacturing methods described in Example 1, except that the casting material used for the adapter also was "TDT 178-34" urethane casting resin commercially available also from Ren Plastics. The durometer of the adapter was measured according to the method described in Example 1. The durometer of this adapter was 40 Shore A.

EXAMPLE 3

An adapter was fabricated according to the methods of manufacture in Example 1, except that the casting material used was "RP 6402" urethane casting resin commercially available from Ren Plastics. The durometer of the adapter was measured according to the method described in Example 1. The measured durometer was 80 Shore A.

EXAMPLE 4

An adapter of the alternate embodiment shown in FIG. 3 was fabricated by the methods of manufacture described in Example 1 above, except that an annular bore of 8 mil (0.02 cm) was formed on the surface of raised boss 18 defining central opening 16 by cutting a groove in the male mold. An auxiliary diaphragm 22 of 8 mil (0.02 cm) thick epoxy resin-fiberglass laminate was popped into the male mold. This male mold with diaphragm was then covered with liquid resin forming a first female mold portion corresponding to the outer surface of the male mold. After 12 hours at room temperature, that structure was inverted and a second female mold portion was cast corresponding to the inner surface of the male mold. The male mold was then removed and an auxiliary diaphragm was adhered to the generally flat section of the second female mold portion which had been adjacent to the auxiliary diaphragm in the male mold during the formation of the second female mold portion. The first female mold portion was filled with resin and the second female mold portion was positioned inside the first female mold portion, displacing a quantity of the liquid resin. After 12 hours, the female mold was disassembled and the adapter with auxiliary diaphragm was removed.

EXAMPLE 5

This example describes the comparison of sound intensity to frequency using a stethoscope without an adapter according to the present invention, and with that stethoscope having two different adapters releasably engaged therewith.

A "Littmann TM" brand model 2160 tunable stethoscope commercially available from Minnesota Mining and Manufacturing Company of St. Paul, Minn. was measured in the frequency range from 0 to 1,000 Hz. Sufficient pressure, about 200 grams, was applied to the stethoscope head to enable the tunable diaphragm microphone to be operating in its low frequency mode. A adapter prepared according to Example 1 was releasably placed over the diaphragm microphone of the stethoscope head. Again, the stethoscope head had sufficient pressure applied thereto in order to operate in a low frequency mode. The sound intensity was measured in the frequency range from 0 to 1,000 Hz.

The adapter prepared according to Example 1 was removed from the stethoscope head and an adapter prepared according to Example 2 was placed on the stethoscope head in the same manner as that for Example 1. Again, the stethoscope head had such pressure applied as to be operating in its low frequency mode and the intensity was measured throughout the frequency range from 0 to 1,000 Hz.

Figure 7:
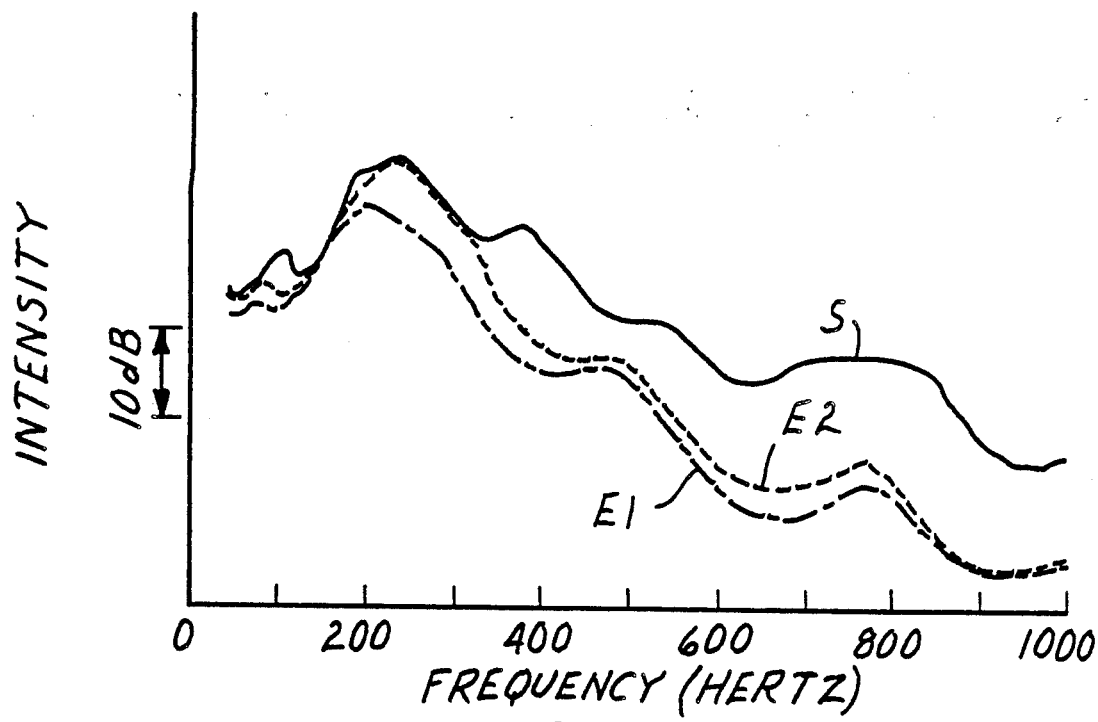
FIG. 7 is a graph of sound intensity to frequency comparing a stethoscope head without an adapter with two different head-adapter combinations.

FIG. 7 is a graph comparing the sound intensity to the frequency range for each of the three measurements made according to this example to determine relative attenuation of sound. Solid line S is the measurement of intensity to frequency for the stethoscope head without any adapter. Intermittent line E1 is the measurement of intensity to frequency for the stethoscope head having the adapter of Example 1. Dotted line E2 is the measurement of intensity to frequency for the stethoscope having the adapter prepared according to Example 2.

Analysis of the three measurements indicated that in the range from 125 to about 175 Hz, within which both sounds of normal heart valve operation are present, neither adapter substantially altered the attenuation profile of the stethoscope's diaphragm microphone. Additionally, the adapter of Example 2 did not substantially alter the attenuation profile of the stethoscope's diaphragm microphone between 200 and 350 Hz where the acoustical energy of many types of murmurs is located. In contrast, above 350 Hz, stethoscopes having adapters of Examples 1 or 2 dramatically increased the attenuation of sound transmission compared with attenuation of such sound by the stethoscope alone. The extraneous noises including ambient room sounds found in the frequencies above about 350 Hz are much quieter to the listener when either adapter of Example 1 or adapter of Example 2 is used in combination with the stethoscope. Because the only difference between the adapter of Example 1 and the adapter of Example 2 is the durometer of 70 Shore A and 40 Shore A, respectively, selection of the casting material to achieve a particular durometer of the adapter so molded provides a difference of intensity to frequency in the diagnosing frequency range of 75 to 350 Hz. For example, the adapter of Example 1 excludes more noise in the range of 75 to 350 Hz while the adapter of Example 2 more closely follows the pattern of sound a listener is accustomed to hearing, until about 350 Hz. Thus, it is a matter of selection between adapters of these two durometers as to the particular pattern of frequency attenuation desired within as well as without the desired frequency range.

EXAMPLE 6

The intensity versus frequency measurements to determine relative sound attenuation described in Example 5 were repeated using the same stethoscope and using the adapter prepared according to Example 1. In this example, the second adapter used with the stethoscope head is the adapter prepared according to Example 4 having the secondary diaphragm 22 in the annular bore 24.

Figure 8:
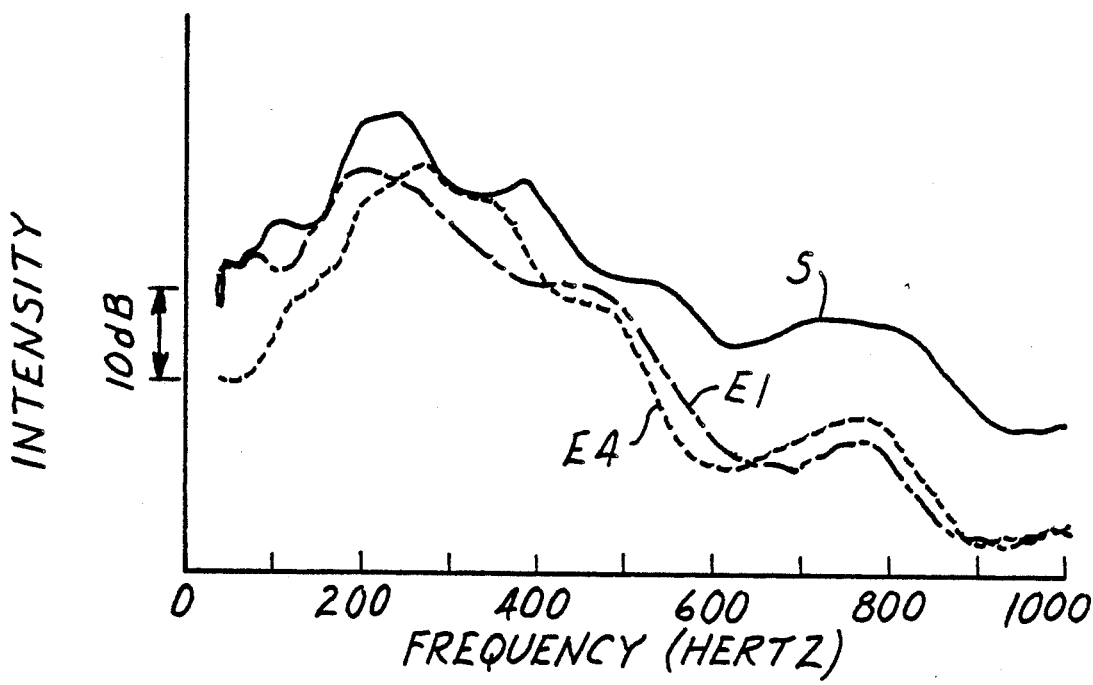
FIG. 8 is a graph of sound intensity to frequency comparing a stethoscope head without an adapter with a stethoscope head having an adapter of one embodiment of the present invention and a stethoscope head having an adapter of another embodiment of the present invention.

FIG. 8 shows the results of the acoustical measurement. The lines for stethoscope head alone (S) and the stethoscope head in combination with adapter made according to Example 1 (E1) are quite similar to the measurements taken in Example 6 and shown in FIG. 7. The stethoscope with the adapter prepared according to Example 4 is shown in the dotted line in FIG. 8. This combination shown by dotted line E4 provides much greater attenuation of sound at all frequencies other than about 250 Hz to about 350 Hz when compared with the attenuation measurement for the stethoscope without any adapter. Thus, the use of a stethoscope with an adapter made according to Example 4 focuses the responsiveness of the diaphragm microphone at those frequencies most desired by the listener to diagnose pathological conditions in the range of 250 Hz to 350 Hz, such as high frequency heart murmurs, fine crackles produced by the lungs, and the like.

Because the only difference between the adapter prepared according to Example 1 and the adapter prepared according to Example 4 is the presence of secondary diaphragm 22 and annular bore 24, FIG. 8 shows the differences achieved by the placement of a secondary diaphragm in the adapter 10 in the raised boss 18. This example also demonstrated how it was possible to "fine tune" the reception of the diaphragm microphone to those frequencies most desired by the listener.

While certain embodiments of the present invention have been described in detail above and shown in the drawing, it is understood by those skilled in the art that various other modifications are possible without departing from the scope of the invention.

What is claimed is:
1. A stethoscope head, comprising:
   a body surrounded by a releasable engagment perimeter,
   a diaphragm residing in said body and having a sound receiving surface area within said perimeter, and
   an adapter releasably engaging said perimeter, said adapter comprising a perimeter engaging edge portion, a cover portion extending from said edge portion, and a rim at which said cover portion terminates to define a central opening having an area less than said sound receiving surface area.

2. A stethoscope head, according to claim 1, wherein said rim comprises a raised boss extending from said cover portion.

3. A stethoscope head, according to claim 2, wherein said raised boss has an annular bore therein and wherein said adapter further comprises a secondary diaphragm residing in said annular bore.

4. A stethoscope head, according to claim 1, wherein said edge portion has an annular lip engaging said perimeter.

5. A stethoscope head, according to claim 1, wherein said cover portion of said adapter is elastomeric having a Shore A durometer of from about 10 Shore A to about 90 Shore A.

6. A stethoscope head, according to claim 5, wherein said cover portion of said adapter has a Shore A durometer of from about 20 Shore A to about 80 Shore A.

7. A stethoscope head, according to claim 6, wherein said cover portion of said adapter has a Shore A durometer of from about 35 Shore A to about 75 Shore A.

8. A stethoscope head, comprising:
a body bounded by a releasable engagement perimeter; a diaphragm in said body having a diaphragm sound receiving surface area; and an adapter releasably engaging said perimeter and having a cover terminating in a central opening having an area less than said diaphragm sound receiving surface area.

9. An adapter for a diaphragm stethoscope head having a diaphragm sound receiving surface area at the diaphragm surrounded by a perimeter, said adapter comprising:
a head engaging edge portion adapted to releasably engage the perimeter, a cover portion extending from said edge portion, and a rim at which said cover portion terminates to define a central opening having an area less than the diaphragm sound receiving surface area.

10. An adapter, according to claim 9, wherein said rim comprises a raised boss extending from said cover portion.

11. An adapter, according to claim 10, wherein said raised boss has an annular bore therein and wherein said adapter further comprises a secondary diaphragm residing in said annular bore.

12. An adapter, according to claim 9, wherein said edge portion has an annular lip engaging the head.

13. An adapter, according to claim 9, wherein said adapter is elastomeric having a Shore A durometer of from about 10 Shore A to about 90 Shore A.

14. An adapter, according to claim 13, wherein said adapter has a Shore A durometer of from about 20 Shore A to about 80 Shore A.

15. An adapter, according to claim 14, wherein said adapter has a Shore A durometer of from about 35 Shore A to about 75 Shore A.

16. An adapter, according to claim 13, wherein said adapter comprises a urethane or a silicone elastomer.

17. An adapter, according to claim 9, wherein said edge portion comprises one material having a Shore A durometer in excess of 10 Shore A and said cover portion comprises an elastomer having a Shore A durometer of from about 10 Shore A to about 90 Shore A.

18. A stethoscope, comprising:
a sound receiving head having a body and a stem having a bore therein,
said body surrounded by a releasable engagement perimeter;
a diaphragm residing in said body and having a central aperture in communication with said bore;
said diaphragm having a diaphragm sound receiving surface area within said perimeter;
sound transmitting tubing having at least one lumen and connected to said stem, wherein said lumen is in communication with said bore; and
an adapter releasably engaging said perimeter, said adapter comprising a diaphragm cover with a central opening having an area less than said diaphragm sound receiving surface area.

19. A stethoscope, according to claim 18, wherein said cover has a secondary diaphragm residing across said central opening.

20. A stethoscope, according to claim 18, wherein said diaphragm is responsive to pressure, enabling tuning of said diaphragm to specific ranges of sound frequencies.

21. A stethoscope, according to claim 18, wherein said adapter is elastomeric having a Shore A durometer of about 10 Shore A to about 90 Shore A, whereby said adapter attenuates sound frequencies other than said specific ranges of sound frequencies substantially more than said specific ranges of sound frequencies are attenuated.

* * * * *